United States Patent
Shalaby

(10) Patent No.: US 7,371,256 B2
(45) Date of Patent: May 13, 2008

(54) COMPOSITE VASCULAR CONSTRUCTS WITH SELECTIVELY CONTROLLED PROPERTIES

(75) Inventor: Shalaby W Shalaby, Anderson, SC (US)

(73) Assignee: Poly-Med, Inc, Anderson, SC (US)

( * ) Notice: Subject to any disclaimer, the term of this patent is extended or adjusted under 35 U.S.C. 154(b) by 339 days.

(21) Appl. No.: 10/735,063

(22) Filed: Dec. 12, 2003

(65) Prior Publication Data

US 2004/0171978 A1   Sep. 2, 2004

Related U.S. Application Data

(60) Provisional application No. 60/433,854, filed on Dec. 16, 2002.

(51) Int. Cl.
*A61F 2/06* (2006.01)
*A61F 13/00* (2006.01)

(52) U.S. Cl. ..................... 623/1.42; 424/2.11
(58) Field of Classification Search ...... 427/2.12–2.31; 424/450, 422; 623/1.38–1.54
See application file for complete search history.

(56) References Cited

U.S. PATENT DOCUMENTS

| | | | |
|---|---|---|---|
| 3,940,377 A | * | 2/1976 | Horowitz et al. ............ 525/344 |
| 4,670,146 A | * | 6/1987 | Inoue et al. ................ 210/490 |
| 5,869,127 A | * | 2/1999 | Zhong ........................ 427/2.12 |
| 2003/0059463 A1 | * | 3/2003 | Lahtinen ..................... 424/450 |
| 2003/0147935 A1 | * | 8/2003 | Binette et al. .............. 424/423 |
| 2003/0216524 A1 | * | 11/2003 | Bide et al. .................. 525/418 |
| 2005/0058692 A1 | * | 3/2005 | Hai-Quan et al. .......... 424/443 |

FOREIGN PATENT DOCUMENTS

| EP | 04/77979 A2 | 1/1992 |
|---|---|---|
| WO | WO 01/41821 A1 | 6/2001 |

OTHER PUBLICATIONS

Kawamura et al., "Stimulatory effect of zinc-releasing calcium phosphate implant on bone formation in rabbit femora," (2000), pp. 184-191.

Lee et al., "Enhanced bone formation by controlled growth factor delivery from chitisan-based biomaterials," Journal of Controlled Release, (2002), pp. 187-197, 78.

Wang, "Developing bioactive composite materials for tissue replacement," Biomaterials, (2003), pp. 2133-2151, 24.

* cited by examiner

*Primary Examiner*—Suzette Gherbi
(74) *Attorney, Agent, or Firm*—Leigh P Gregory

(57) ABSTRACT

This invention deals with a composite vascular construct, which is formed of a first, blood contacting component and a second, tissue contacting component. Preferably, the present vascular constructs are in the form of a vascular patch or vascular graft with surface-activated, non-absorbable fabric with immobilized biomolecules on the blood contacting surface, and an absorbable, compliant film or microporous sheath on the other surface of the non-absorbable component of the composite graft or patch.

8 Claims, No Drawings

COMPOSITE VASCULAR CONSTRUCTS WITH SELECTIVELY CONTROLLED PROPERTIES

This application claims the benefit of prior provisional application Ser. No. 60/433,854, which was filed on Dec. 16, 2002.

BACKGROUND TO THE INVENTION

Most common among synthetic vascular constructs are vascular grafts. However, there has been a steady increase in the development of some allied constructs such as vascular wraps, patches, and endovascular stent grafts. Most of the design criteria used in the development of useful vascular grafts are usually applicable for other forms of vascular constructs in spite of noticeable differences in end-use requirements. Since the use of Vinyon N cloth (made of a copolymer of vinyl chloride and acrylonitrile) by Voorhees and coworkers in 1952, as a tubular construct for bridging arterial defects, many investigations have been directed toward the development of synthetic vascular grafts. Of the many systems investigated, Polyethylene terephthalate (PET) and polytetrafluoroethylene (PTFE) are the most commonly used polymers. Needless to say, limited attention was given to vascular patches or wraps, which can be made from similar materials as those of the vascular grafts, but which are used less frequently than the grafts.

Although PTFE and PET vascular grafts, having a diameter of more than 6 mm, have been clinically successful, development of clinically acceptable, small diameter grafts has been generally unsuccessful. Thrombus and neointima formation will readily occlude the small diameter synthetic vascular grafts. The resulting loss of patency remains the greatest obstacle to the development of a small caliber vascular prosthesis. Thus, there is a need for an engineered material that will provide the necessary mechanical and thromboresistant properties for a successful synthetic vascular prosthesis to facilitate recent advancements in vascular surgery.

During the many attempts made in the prior art toward the development of small diameter grafts, special attention has been given to (1) improving the biomechanical compatibility of the graft; (2) modifying the luminal surface to minimize platelet aggregation and subsequent thrombosis; and (3) pre-seeding the luminal wall with endothelial cells to provide a more natural environment to the blood component and to normalize the blood flow in the grafts.

Since Voorhees and coworkers (1952) first used Vinyon "N" cloth as a vascular graft and their conclusion that synthetic materials could serve as conduits, development in this area did not keep pace with impressive advances in materials and medical device technologies. Meanwhile, the considerable health concerns associated with vascular diseases and inadequate supply of native vessels for bypass procedures have led to the development of synthetic vascular grafts made from expanded polytetrafluoroethylene (PTFE), polyethylene terephthalate (PET) or polyurethane (PU), which satisfies the need for large size vascular grafts with patency approaching those of autologous grafts. However, the synthetic, small-diameter grafts are yet to match the autologous grafts in terms of long-term patency. For the past twenty years, no major developments have been accomplished in this area in spite of the recent rush to exploit new findings associated with tissue engineering. This may be attributed to the fundamental disconnect between highly focused areas of the academic vascular research and industrial efforts where interests broadly extend from abstract cell biology and tissue engineering to short-term, applied vascular research. It is well acknowledged that functional failures of synthetic vascular grafts are associated with (1) loss of patency due to platelet aggregation and subsequent thrombosis; (2) delayed or inadequate surface endothelialization; (3) blood leakage and/or mechanical failure due to improper graft construction and/or biomechanical properties; and (4) infection, which may be traced to compromised graft sterility. Unfortunately, in addressing these failure modes, individual investigators (1) addressed one particular mode and practically ignored others, which can affect the collective performance during in-use applications; (2) rushed to use extreme animal models in early stages of graft evaluation, which can obliterate simple findings leading to hasty interpretation of results and failure when tested in humans; and/or (3) rushed to rely heavily on tissue engineering as the solution for existing problems without acknowledging the lengthy process required to provide a prototype graft. Needless to say, a novel approach to address the issue of vascular graft failures is needed. Such an approach is expected to (1) address the different modes of graft failure in a collective manner and to provide an integrated solution to the root causes of these failures; and (2) use existing knowledge of tissue engineering in tandem with established principles of bioengineering and device design, while taking advantage of advances made in the development of transient bioabsorbable implants.

SUMMARY OF THE INVENTION

Accordingly, the present invention is directed to a composite vascular construct in the form of a vascular patch or graft comprising a blood-contacting load-bearing component responsible, in part, for providing its mechanical strength and a second component, which is responsible primarily for controlling mass transport across the composite construct. The blood-contacting component comprises a surface-activated fabric comprising a non-absorbable fiber such as those made of polypropylene. The surface activation of this component can entail the steps of surface sulfonation, and then treating with basic molecules, such as polylysine, upon which biomolecules, such as albumin or fibrinogen, are immobilized with minimum or no change in conformation to insure maximum blood biocompatibility. The second component of the composite vascular construct is made of an absorbable polymer that can provide a barrier or occlusive properties and/or allow for tissue ingrowth. The absorbable component of the vascular construct can be in the form of a film or microporous sheath. The latter can be a continuous-cell foam or non-woven micro-/nano-fibers made by electrospinning. The absorbable component of the vascular construct may also contain one more bioactive agent that promotes healing and/or tissue ingrowth. The bioactive agents are exemplified by cell growth promoters, growth factors, or their respective peptide analogs.

Thus, more specifically, the present invention is directed to a composite vascular construct which has a first, blood-contacting component and a second, tissue-contacting component, wherein the first component is a load bearing textile construct having an activated, blood compatible surface and the second component is an absorbable construct for tissue ingrowth, and wherein at least one of the first and second components has at least transient occlusive properties. In a preferred embodiment the first component is a polypropylene fabric, preferably woven or knitted, having a biomolecule, such as albumin or fibrinogen, immobilized on the blood-contacting surface thereof. It is also preferred that the blood-contacting surface of the first component has sulfonic groups formed thereon such that the biomolecule which is immobilized on the surface is actually ionically bound to a basic molecule, such as polylysine, which is ionically bound to the sulfonic groups. In another preferred embodiment the first component is a non-absorbable textile construct formed of fibers such as polyester, polyether ester, polyether ether ketone, or polyamide, which includes immobilized biomolecules on the blood-contacting surface thereof.

Preferably the second component is a compliant, absorbable film having transient occlusive properties. A preferred film is a copolyester having repeat units derived from two or more cyclic monomers such as caprolactone, p-dioxanone, glycolide, lactide, trimethylene carbonate, 1,-5 dioxepan-2-one, morpholinedione, or a substituted morpholinedione. It is preferred that the tissue-contacting surface of the absorbable film includes at least one bioactive compound, such as a cell growth promoter. In another preferred embodiment the second component is a compliant, absorbable, microporous sheath, preferably a continuous cell foam or a non-woven nano/microfabric. For such embodiment it is preferred that the tissue-contacting surface of the microporous sheath includes a bioactive agent, such as a growth factor. The present composite vascular construct may be employed as, for example, a vascular graft, a vascular patch, or an endovascular stent graft.

DETAILED DESCRIPTION OF THE PREFERRED EMBODIMENTS

Generally, the present invention is directed to a composite vascular construct of at least two types of chemically different synthetic polymers and two physicochemically different surfaces, that is, a first, blood contacting component and a second, tissue contacting component. Preferably, the first component has a blood compatible blood-contacting surface and provides mechanical strength. One of the two components must provide occlusive, i.e., blood barrier, properties, or at least transient occlusive properties. Specifically, if the second component, which is absorbable in order to allow for tissue ingrowth, is the only component having occlusive properties, then those properties will be compromised as the component loses mass with time and eventually degrades. Therefore, such occlusive properties are considered to be transient.

The first component, which for most embodiments is intended to provide the needed mechanical strength for the composite, can be made of non-absorbable fibers of polymers such as polypropylene, polyethylene terephthalate, polyethylene, polyether-ether ketone, polyamide, such as Nylon 12, or any other non-absorbable, high strength fibers with similar properties to those made of such polymers. The first component intended for providing the needed mechanical strength to the composite can also include absorbable fibers of polymers such as those derived, fully or in part, from one or more of the following cyclic monomers: lactide, glycolide, p-dioxanone, trimethylene carbonate, $\epsilon$-caprolactone, 1,5-dioxepan-2-one, substituted or unsubstituted 1,5-morpholinedione. The mechanical supportive component of the composite construct can be made of composite yarn and mixed yarn of the non-absorbable and absorbable type noted above. This is to create a partially absorbable scaffold, which is responsible for providing full mechanical support at the initial periods of implantation and gradually decreasing its mechanical support as the absorbable yarn (or fiber) degrades with time, thus allowing for slowly transferring part of the mechanical loading to natural tissue growing into the framework of the composite graft.

In most embodiments the second component is not expected to contribute significantly to the mechanical strength of the composite, but it is intended to impart occlusive or barrier properties and also allow tissue ingrowth into the construct. For imparting the barrier or occlusive properties, it is preferred that the second component is formed of a highly compliant, absorbable polymer. It functions as a backing to the first component, which is the mechanically responsible fabric scaffold of the construct. Thus, the second component provides the initial barrier properties to prevent blood leakage and gradually absorbs and allows natural tissue to integrate with the outside surface of the fabric scaffold. The occlusive component of the composite can be made of a highly compliant polymer made of one or more of the following cyclic monomer: lactide, caprolactone, p-dioxanone, glycolide, trimethylene carbonate, 1,5-dioxepan-1-one, p-dioxanone, and substituted or unsubstituted morpholinedione. Such polymers will provide initial barrier properties but will absorb to allow for tissue ingrowth. To accelerate or encourage tissue ingrowth into components of the composite construct, bioactive agents, including cell growth promoters or factors, can be incorporated in the absorbable component.

The present composite vascular construct consists of an internal, luminal wall, or blood-contacting surface, and an external surface abutting the surrounding tissue about the construct. The luminal, or internal surface, is physicochemically unique in terms of its ability to prevent platelet aggregation and promoting endothelialization. To attain such a unique internal surface, the fibrous scaffold will be first treated (as per Example 1) with fuming sulfuric acid in a suitable medium to create anion-forming groups that are covalently bonded to the fibers as in the case of sulfonic groups. The anion-forming surface is then neutralized with an organic base, or polycations such as polylysine, so as to infer a net positive charge on the surface. This, in turn, is allowed to immobilize one, or more, biocompatible protein with minimum or no change in its conformation. Typical examples of such protein are serum albumin and fibrinogen, or any other types of proteins, polypeptides, or oligopeptides that are capable of providing a similar function. The external surface of the occlusive film may be modified by, for instance, sulfonation to bind one, or more, growth factor that accelerates tissue ingrowth. The external surface of the composite construct is, in effect, the outside surface of the absorbable component interfacing with the surrounding tissue. And the external surface of the construct of the occlusive film is intended to be biocompatible without requiring an imparted charge, or so modified with anion-forming groups and then cation-forming surfaces, to encourage integration with surrounding tissue and hence, facilitate the stabilization of the construct at the application site.

In one preferred embodiment the present invention is directed to a vascular patch made of surface-modified polypropylene fabric comprising an immobilized biomolecule at the blood-contacting surface and occlusive, compliant, absorbable film at the other surface of the polypropylene fabric. The surface modified polypropylene or other non-absorbable polymer, such as a polyamide (e.g., Nylon 12), polyether ether ketone or polyethylene terephthalate, is first sulfonated and then allowed to ionically bind a basic molecule, such as polylysine, upon which is further immobilized a biomolecule, such as albumin or fibrinogen. The composite vascular construct can be in the form of an arterial or vascular patch and also a vascular or arterial graft.

Another aspect of this invention deals with a vascular patch with a surface activated blood-contacting component and second component interfacing with tissue at the application or implantation site that is an occlusive, compliant, absorbable film is made of a copolyester comprising repeat units derived from two or more of the following cyclic monomers: caprolactone, p-dioxanone, glycolide, lactide, trimethylene carbonate, 1,-5 dioxepan-2-one, morpholinedione, and a substituted morpholinedione.

One aspect of this invention deals with a composite vascular construct comprising a component responsible primarily for providing the mechanical strength of the construct, which can be in the form of a woven or knitted fabric. Meanwhile, a second component abutting the tissue at the surgical site, that is made of an absorbable material, and can be in the form of (a) a barrier film; (b) a microporous foam or sheath; and (c) non-woven sheath comprising micro-/nano-fibers applied on the interior component by electro-spinning.

A specific aspect of this invention deals with a vascular construct in the form of a venous patch comprising a knitted polypropylene fabric that is subjected to (1) sulfonation; (2) binding polylysine to the sulfonic acid-bearing surface; (3) adjoining a compliant copolyester film to the knitted fabric on one side; (4) sterilizing the composite construct; and (5) aseptically binding the serum albumin or fibrinogen to the surface of the knitted fabric opposite, to the occlusive backing. Another aspect of this invention deals with a vascular construct in the form of an arterial patch, with similar design to the venous patch, with the exception of using the proper fibers and construction to withstand higher pressures than those encountered by the venous patch. Another specific aspect of this invention deals with a composite construct in the form of a vascular graft having a diameter of at least 4 mm. Another specific aspect of this invention deals with a vascular construct in the form of an endovascular graft.

A special aspect of this invention deals with (1) a novel surface-modified construct to permit protein deposition with minimum or no conformational changes to reduce or minimize platelet aggregation while facilitating surface endothelialization; (2) using a biomechanically compatible, partially absorbable composite construct to allow long-term mechanical stability and provide short-term occlusive properties followed by tissue ingrowth to stabilize the patch (through in situ tissue engineering); and (3) the identification of an attachment protocol that can be adapted in the development of venous patches, arterial patches, and vascular grafts.

A specific aspect of this invention deals with a venous patch as a simple, easy-to-optimize device for vascular repair that can provide a primary platform for developing a novel breed of vascular devices. These devices will include arterial patches or wraps, synthetic endovascular stent grafts, and vascular grafts.

Although the technology, subject of this invention, is intended for vascular application, its application can be extended to the development of several forms of patches or wraps that can be used in augmenting and/or repairing other tissues or organs, such as bladder, trachea, and ureter. Another obvious application of the technology, such of this invention, is the development of composite patches for hernial repair.

Another aspect of this invention deals with immobilizing one, or more, bioactive agent to the internal blood-contacting surface, or external surface of the construct, to impart additional, more desirable properties to improve the construct's resistance to infection and maintain natural hemodynamics.

Another aspect of this invention is use of a reliable animal, such as the pig jugular vein model, in the early stages of construct evaluation.

The preferred embodiment can be further illustrated in the following examples.

EXAMPLE 1

Spinning of Multifilament Polypropylene (PP) Yarn and Conversion to Knitted Fabric Fiber grade polypropylene supplied by BP Amoco, Austell, Ga., (Catalog # 6361) is extruded using a ¾ inch multifilament extruder equipped for spin-drawing. The spin-drawing is conducted using a process for producing 3 dpf, 25-filament yarn having a tenacity of about 5 g/d. The yarn's morphological and tensile properties are determined using optical microscopy and an MTS-MiniBionix Universal Tester, Model 858, respectively.

The PP yarn is prepared for knitting using a Lamb circular knitter to produce meshes with variable porosity. The meshes are heat-set and their porosity and burst strength are determined using microscopy and the MTS unit (with an attachment for measuring burst strength), respectively.

EXAMPLE 2

Surface Activation of PP Meshes to Positively Charged Substrates for Anchoring Albumin This is conducted by (1) first, sulfonating the mesh with fuming sulfuric acid in dichloromethane—the surface is analyzed for the presence of the sulfonic group using ESCA; and (2) second, treating the sulfonated mesh with a dilute solution of poly-dl-lysine—the presence of poly-dl-lysine is ascertained using ESCA.

EXAMPLE 3

Preparation and Processing of an Absorbable Film

A flexible film is prepared by end-grafting a polymeric polyaxial initiator with a mixture of 1-lactide and glycolide. The polyaxial initiator geared for end-grafting is prepared by copolymerizing a mixture of caprolactone and trimethylene carbonate in the presence of triethanolamine and stannous octoate as an initiator and catalyst, respectively. Residual monomer is removed by distillation under reduced pressure. The purified polymer is compression-molded into a 50-100 micron film using a heated Laboratory Carver Press. The film is used as an occlusive backing for the PP mesh.

EXAMPLE 4

Assembling the PP Mesh with the Absorbable Occlusive Film, Sterilization and Immobilization of Porcine Serum Albumin (PSA)

The occlusive film is heat-sealed to one side of the PP mesh. The assembled system is radiochemically sterilized using 5 kGy of gamma radiation. The sterilized mesh composite is then incubated in a dilute sterile solution of PSA under aseptic conditions. After drying in an aseptic, inert atmosphere, the treated mesh composite is stored in a hermetically sealed pouch under a dry argon atmosphere. Samples of the packaged mesh composite are analyzed for the presence of albumin on the surface-intended to be blood contacting-using ESCA.

EXAMPLE 5

Preparation of Polypropylene (PP) Knitted Tube

Multifilament yarn is produced as described in Example 1. It is knitted into 6-mm diameter tubes using a circular knitting machine. The tubes are heat-set and their mechanical properties in the radial and axial directions are measured using an MTS Universal Tester. Fabric porosity is measured using microscopy.

EXAMPLE 6

Surface Activation of PP Meshes to Positively Charged Substrate for Anchoring Albumin This is conducted by (1) first, sulfonating the mesh with fuming sulfuric acid in dichloromethane—the surface is analyzed for the presence of the sulfonic group using ESCA; and (2) second, treating the sulfonated mesh with a dilute solution of poly-dl-lysine—the presence of poly-dl-lysine is ascertained using ESCA.

EXAMPLE 7

Preparation of a Crystalline Polyaxial Segment of 30/25/40/5 Copolymer of ε-Caprolactone/Trimethylene Carbonate/l-Lactide Glycolide Copolymer The copolymer is prepared using trimethylolpropane and stannous octanoate as the monomeric initiator and catalyst, respectively, using a similar reaction scheme to those reported earlier (Shalaby, U.S. Pat. No. 6,342,065, 2002). Isolation, purification, and characterization methods, similar to those used in U.S. Pat. No. 6,342,065, are utilized to obtain pure crystalline compliant polymer.

EXAMPLE 8

Electrostatic Spinning of Segmented Copolymer onto Surface-Activated

PP Knitted Mesh Tube

The surface-modified PP mesh tube from Example 6 is inverted with the albumin-rich surface becoming its luminal surface. A stainless steel, highly polished rod (or mandrill) is inserted into the tube. The coated mandrill is used as the receiving substrate in an electrostatic spinning process similar to that described by Taylor et al (Transaction, Society of Biomaterials, 2004, in press). For this, a solution of the copolymer from Example 7 in dichloromethane is used to deposit a non-woven, electrostatically spun sheath on the rotating mandrill covered with the knitted mesh, following similar processing conditions to those described by Taylor et al (2004). The composite tube or vascular graft is removed and rinsed with sterile water, dried, and refrigerated prior to preparation for sterilization and use in animal studies.

While the disclosed process has been described according to its preferred embodiments, those of ordinary skill in the art will understand that numerous other embodiments have been enabled by the foregoing disclosure. Accordingly, the foregoing embodiments are merely exemplary of the present invention. Modifications, omissions, substitutions and rearrangements may be made to the foregoing embodiments without departing from the invention as set forth in the appended claims.

What is claimed is:

1. A composite vascular construct comprising a first, blood-contacting component and a second, tissue-contacting component, the first component comprising a load bearing textile construct having an activated, blood compatible surface, the activated blood compatible surface presenting a biocompatible protein comprising albumin, wherein the blood compatible surface has sulfonic groups attached thereto, the sulfonic groups are ionically bound to polylysine and the albumin is ionically bound to the polylysine, the second component comprising an absorbable construct for tissue ingrowth, wherein at least one of the first and second component has at least transient occlusive properties.

2. A composite vascular construct as set forth in claim 1 wherein the first component comprises a polypropylene fabric.

3. A composite vascular construct as set forth in claim 2 wherein the polypropylene fabric comprises a knitted polypropylene fabric.

4. A composite vascular Construct as set forth in claim 1 in the form of a vascular graft.

5. A composite vascular construct as set forth in claim 1 wherein the second component comprises a compliant, absorbable, microporous sheath.

6. A composite vascular construct as set forth in claim 5 wherein the microporous sheath comprises a non-woven nano/microfabric.

7. A composite vascular construct as set forth in claim 5 wherein the tissue-contacting surface of the microporous sheath comprises at least one bioactive agent.

8. A composite vascular construct as set forth in claim 5 wherein the tissue-contacting surface of the microporous sheath comprises at least one growth factor.

* * * * *